United States Patent [19]

Hieber

[11] Patent Number: 5,339,656
[45] Date of Patent: Aug. 23, 1994

[54] EARRING

[76] Inventor: Fritz Hieber, Gunzenbachstr. 33b, 7570 Baden-Baden, Fed. Rep. of Germany

[21] Appl. No.: 1,507

[22] Filed: Jan. 6, 1993

[51] Int. Cl.5 .......................... A44C 7/00; A61N 1/00
[52] U.S. Cl. .................................. 63/14.1; 606/204
[58] Field of Search ................. 63/14.1, 14.2, 14.3, 63/14.4; 606/204; 607/55, 75

[56] References Cited

U.S. PATENT DOCUMENTS

| 490,679 | 1/1893 | Price | 128/789 |
|---|---|---|---|
| 788,770 | 5/1905 | Hill et al. | 63/14.3 |
| 3,739,599 | 6/1973 | Melone | 63/14.3 |
| 4,704,878 | 11/1987 | Saraba | 63/14.1 |
| 4,724,684 | 2/1988 | Barnett | 63/14.1 |
| 5,097,682 | 3/1992 | Nakamura | 63/14.1 |
| 5,146,768 | 9/1992 | Dichtel | 63/14.2 |
| 5,176,009 | 1/1993 | Lang | 63/14.1 |

*Primary Examiner*—Michael Milano
*Attorney, Agent, or Firm*—Klaus J. Bach

[57] ABSTRACT

In an earring for the stimulation of acupuncture points and lines present in the human outer ear which consists of an open-ended annular body of a plastic material having a front end adapted to be received in the outer ear cavity of a wearer and a rear end abutting the rear surface of the outer ear wherein the areas in contact with the outer ear are electrically interconnected and consist of materials which in accordance with their locations in the electrochemical voltage series, provide for a potential and current flow thereacross for the stimulation of the acupuncture points and lines in the outer ear of the wearer of such an earring.

9 Claims, 2 Drawing Sheets

EARRING

BACKGROUND OF THE INVENTION

The present invention relates to an earring for the stimulation of acupuncture points and lines present in the outer ear which consists of an open-ended annular decorative member of any shape whose front end is adapted to be received in the outer ear cavity while its opposite end is abutting the rear surface of the outer ear. The earring may have a decorative structure exposed in front of the outer ear and having its rear end extending along the rear surface of the outer ear wherein the areas of the earring in contact with the outer ear consist of materials, preferably metals, which provide for an electric potential therebetween in accordance with their location in the electrochemical voltage series.

As explained in applicant'earlier U.S. Pat. (Ser. No. 07/827,469 now U.S. Pat. No. 5,176,009) such earrings provide; as a result of the different material in the contact areas with the acidic coating of the skin of a person wearing the earring, a galvanic element generating a constant flow of current resulting in acupuncture effects. In this case, the front end contact point of the earring is located within the outer ear cavity whereas the other end contact point at the rear surface of the outer ear can be selected as desired. This permits to provide for contact with acupuncture, points which cannot normally be accessed by the usual earrings of circular shape.

In accordance with their intended use such therapeutic earrings have generally been made of precious metals in order to avoid irritation of the skin areas in contact with the earrings, particularly to avoid allergic reactions. As a result of the use of such expensive metals, such earrings have been relatively expensive. Also manufacture of these metallic earrings has been relatively expensive particularly since it was necessary to provide different material structures at one end of the earring. In order to avoid high costs it has already been proposed in the aforementioned U.S. Patent to cast the earring in bronze with an iron end piece cast into the earring.

However, even this reasonably inexpensive procedure is still too expensive to make such therapeutic earrings accessible to the population at large. It is therefore the object of the present invention to provide an earring of the type described above which can be manufactured so inexpensively that it is in the price range of normal fashion jewelry pieces which have no therapeutic values.

SUMMARY OF THE INVENTION

A therapeutic earring for the stimulation of acupuncture points and lines present in the human outer ear consists of an open-ended annular body of plastic which has a front end adapted to be received in the outer ear cavity of a wearer and a rear end in contact with the rear surface of the outer ear. The areas of contact with the outer ear are electrically interconnected and consist of materials which, in accordance with their locations in the electrochemical voltage series, provide for a potential and current flow across the ear tissue for stimulation of the acupuncture points and lines in the outer ear of the wearer.

Accordingly the earring no longer consists of an expensive material, that is, of a precious metal, particularly gold, but of an inexpensive plastic which is subsequently, by application of various materials, treated so that it provides for the desired effects. The plastic earring body may, for example, be galvanically coated so as to be electrically conductive wherein the coating may be only very thin since it has to carry only very low current flow and the coating may consist of such materials which, with respect to another material, provide for the desired potential. It is possible to select as contact areas the ends of the open-ended circularly shaped earring which are electrically interconnected by the coating. At least at one of the contact areas a layer of a desired material may be provided by vapor deposition or by a sleeve disposed over the electrically conductive coating. Contact areas may be provided at the opposite ends of the earring and additional contact areas may be provided by metal deposits on the electrically conductive coating in various areas of the earring in contact with acupuncture points on the outer ear.

The earring may also be manufactured very inexpensively without a full conductive coating by placing metallic sleeves over the ends of the ring body or at least one end of the ring body wherein the ends are provided with metals which are electrically interconnected and between which a groove is provided at the contact area with the outer ear so that at this point together with the electrolyte present in the outer ear cavity a galvanic element is formed which generates the desired effects in this contact area. Preferably gold and iron are used as the two materials providing for the voltage potential.

It is further within the scope of the present invention that the plastic material of which the earring body consists itself is electrically conductive and, in this manner, is capable of electrically interconnecting the earring's contact areas. Also, the earring body may be hollow and filled with an electrically conductive fluid, such as salt water, which extends between the contact areas within the earring body. Further, the earring body may be hollow with a wire extending through the interior and interconnecting the contact areas or such wire may be molded into the earring body.

DESCRIPTION OF PREFERRED EMBODIMENTS

Figure 1:
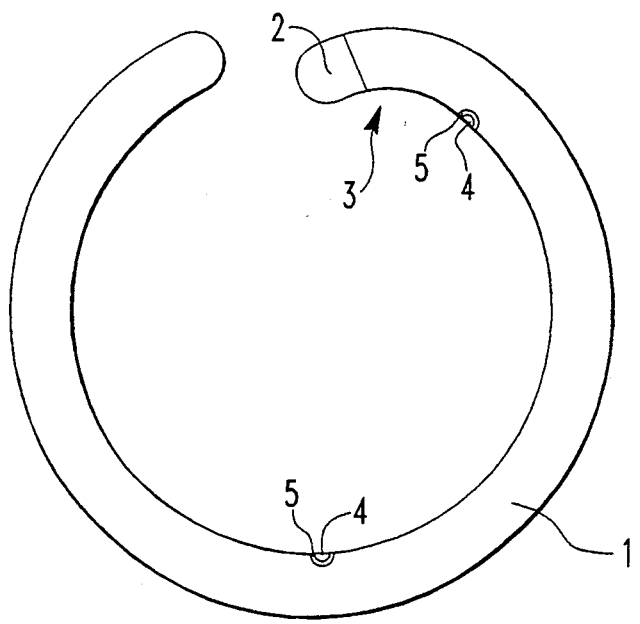
FIG. 1 shows schematically one embodiment the earring.
Figure 2:
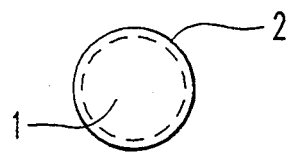
FIG. 2 is a frontal view of a sleeve structure disposed an one end of the earring.

As shown in FIG. 1 an open-ended essentially circular earring 1 consisting of plastic is coated over its whole surface by a coating material which, with regard to the material of which a sleeve 2 consists, that is disposed on one end 3 of the open-ended ring, provides for a potential in accordance with the electrochemical voltage series. The end 3 with the sleeve 2 is bent inwardly slightly to provide for safe seating in the outer ear cavity. Additional material providing for a voltage potential with respect to the coating material of the earring is also provided on other areas of the earring 1 which are in contact with the outer ear tissue of a wearer. This additional material 4 is separated from the coating by an insulating material 5 so that an additional galvanic element is formed there, again in combination with the electrolytes present on the skin of a wearer.

In another embodiment (FIG. 3) in which no coating is required for the earring, a sleeve 12 is provided which consists of two different metals 7, 8 which are separated by a groove 6 and which have relative to one another, a potential according to their relative positions in the electrochemical voltage series. The two metals are separated from one another by a groove so that, here again, a galvanic element is formed in combination with the electrolyte disposed on the skin in the outer ear cavity whereby a current is provided with the corresponding effects on the outer ear tissue in the particular area.

Figure 3:
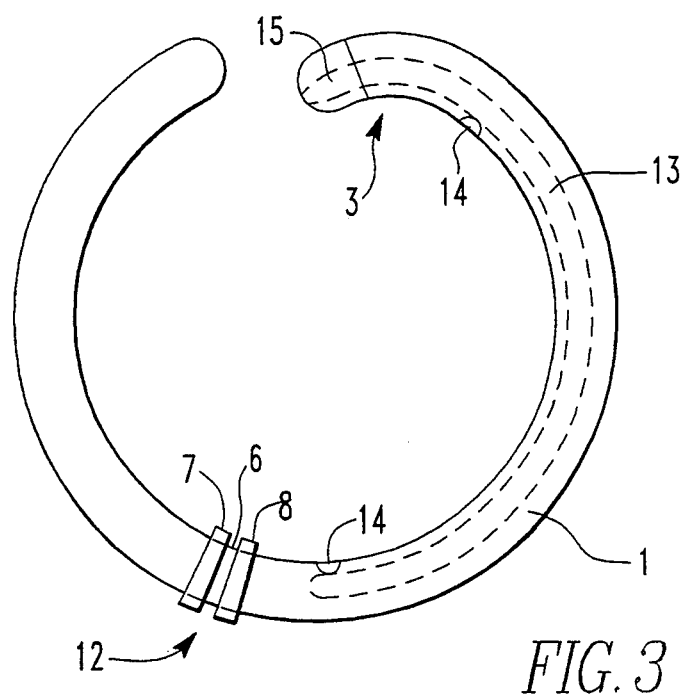
FIG. 3 discloses a hollow earring receiving a conductive fluid.

FIG. 3 shows an earring with a hollow body providing top an inner space 13 which is filled with an electrically conductive fluid. Contact points 14 are provided which are electrically connected to contact point 15 via the conductive fluid in the inner space 13.

Figure 4:
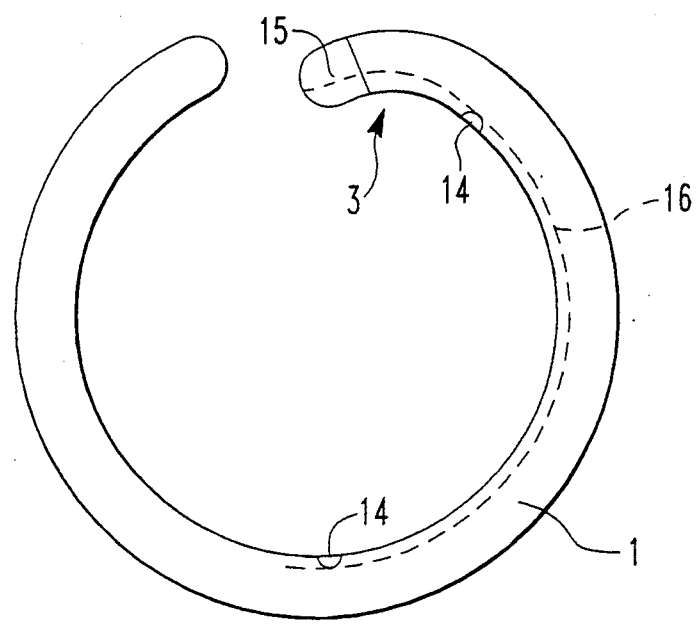
FIG. 4 shows an earring with a connecting wire disposed in its interior.

FIG. 4 shows an earring 1 with a wire 16 molded into the earring body so as to provide top an electrical connection between the contact points 14 and the end contact 15.

What is claimed is:

1. In an earring for the stimulation of acupuncture points and lines present in the outer ear consisting of an open-ended annular body having a front end adapted to be received in the outer ear cavity of a wearer while the other end abuts the rear wall of such outer ear, said earring body having areas in contact with the outer ear consisting of materials which provide for a potential and current flow thereacross, the improvement wherein said annular body consists of plastic provided at said areas of contact with the ear with sleeves mounted onto said open-ended annular body and consisting of materials which have different electrochemical potentials, said sleeves being electrically connected to one another via an electrically conductive coating of said annular body.

2. An earring according to claim 1, wherein said two materials providing said electrochemical voltage potential with regard to one another are gold and iron.

3. An earring for the stimulation of acupuncture points and lines present in the outer ear, consisting of an open-ended annular body of plastic material having a front end adapted to be received in the outer ear cavity of a wearer while the other end abuts the rear wall of such outer ear, said open-ended annular earring body being coated with an electrically conductive material and having disposed at least at one of its contact areas with said ear a sleeve which electrically insulated from said coating and consists of a material which has a different electrochemical potential than said coating so as to provide for voltage potential differences in the areas of contact with the skin of the wearer.

4. An earring for the stimulation of acupuncture points and lines present in the outer ear, consisting of an open-ended annular body of plastic material having a front end with a contact area adapted to be received in the outer ear cavity of a wearer while the other end abuts the rear wall of such outer ear with a contact structure disposed on said annular body at said front end and at least one other area in contact with the skin of a wearer, said open-ended annular earring body including an electrically conductive structure extending through said annular body at least between said front end and said other contact area and being in electrical contact with said contact structures, said contact structures consisting of materials of different electrical potentials so as to provide for voltage differences in the areas of contact of said contact structures with the skin of the wearer.

5. An earring according to claim 4, wherein said body consists of electrically conductive plastic atleast between said front end and said other contact area.

6. An earring according to claim 4, wherein said body is hollow at least between two contact areas providing for an interior space which is filled with an electrically conductive fluid providing for an electrical connection between the contact areas.

7. An earring according to claim 4, wherein said body includes a fire extending between said contact areas so as to provide for an electrical connection between the contact areas.

8. An earring according to claim 4, wherein said contact areas are formed by sleeves mounted onto at least one of the ends of said open-ended annular body.

9. An earring according to claim 8, wherein said sleeve consists of a metal and has disposed thereon in electrical contact therewith a metal member which has an electrochemical voltage potential with regard to the sleeve metal, said metal member being arranged so as to form a gap with said sleeve in the area of contact with the ear of a wearer.

* * * * *